(12) United States Patent  
Berger et al.

(10) Patent No.: US 8,658,996 B2  
(45) Date of Patent: Feb. 25, 2014

(54) COMPUTED RADIOGRAPHY SCANNER AND ENVELOPE FOR IMAGING PLATES

(75) Inventors: Amir Berger, Kiryat Bialik (IL); Amit Schnell, Yokneam (IL)

(73) Assignee: Carestream Health, Inc., Rochester, NY (US)

( * ) Notice: Subject to any disclaimer, the term of this patent is extended or adjusted under 35 U.S.C. 154(b) by 244 days.

(21) Appl. No.: 13/048,156

(22) Filed: Mar. 15, 2011

(65) Prior Publication Data

US 2012/0236998 A1   Sep. 20, 2012

(51) Int. Cl.  
*B65H 5/00*   (2006.01)

(52) U.S. Cl.  
USPC .......................................... 250/589; 250/584

(58) Field of Classification Search  
USPC ............... 250/589, 484.4, 584, 588; 378/191, 378/192, 168–170  
See application file for complete search history.

(56) References Cited

U.S. PATENT DOCUMENTS

| | | | |
|---|---|---|---|
| 4,889,989 A * | 12/1989 | Yoshimura et al. | 250/589 |
| 5,466,561 A * | 11/1995 | Rantanen | 430/347 |
| 6,046,458 A * | 4/2000 | Rantanen | 250/485.1 |
| 6,117,471 A | 9/2000 | King | |
| 6,315,444 B1 | 11/2001 | Koren | |
| 6,827,214 B2 | 12/2004 | Alzner et al. | |
| 6,866,149 B2 | 3/2005 | Alzner | |
| 7,053,396 B2 | 5/2006 | Alzner et al. | |
| 7,211,785 B1 | 5/2007 | Berger et | |
| 7,649,190 B2 | 1/2010 | Alzner et al. | |
| 2003/0128814 A1 * | 7/2003 | Alzner et al. | 378/168 |
| 2003/0147503 A1 * | 8/2003 | Alzner et al. | 378/175 |
| 2004/0238607 A1 * | 12/2004 | Collins | 229/68.1 |
| 2005/0218356 A1 * | 10/2005 | Apajasaari | 250/589 |
| 2005/0232575 A1 | 10/2005 | Koren | |
| 2010/0171052 A1 | 7/2010 | Thoms | |

FOREIGN PATENT DOCUMENTS

DE   10303001   5/2004

OTHER PUBLICATIONS

International Search Report mailed on Sep. 21, 2012 for International Application No. PCT/US2012/024797, 2 pages.

* cited by examiner

*Primary Examiner* — David Porta  
*Assistant Examiner* — Gisselle Gutierrez

(57) ABSTRACT

A scanner for processing intra-oral flexible information carrier plate exposed to X-rays and an envelope for the plate. The scanner comprises housing with an opening for entering an enveloped plate. The envelope is provided with a protrusion and the opening of the scanner is provided with a shoulder. When the enveloped plate is entered in the opening the protrusion abuts the shoulder such that the plate is allowed to exit from the envelope and pass inside the housing while the envelope is retained outside the housing.

18 Claims, 11 Drawing Sheets

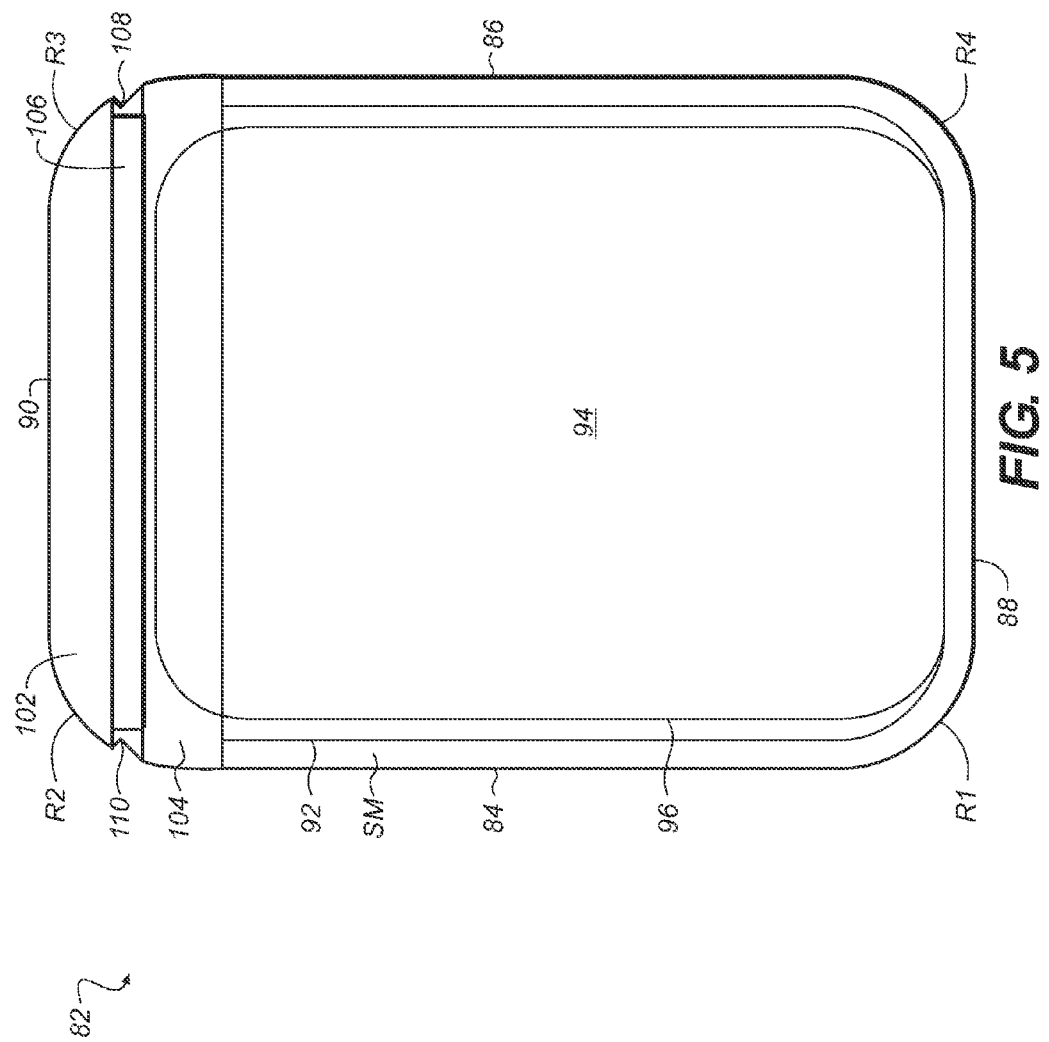

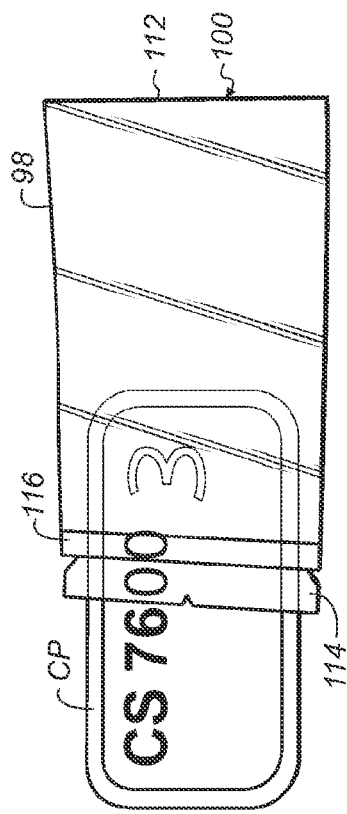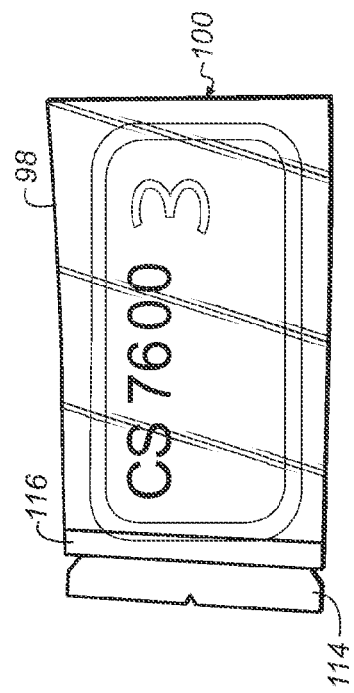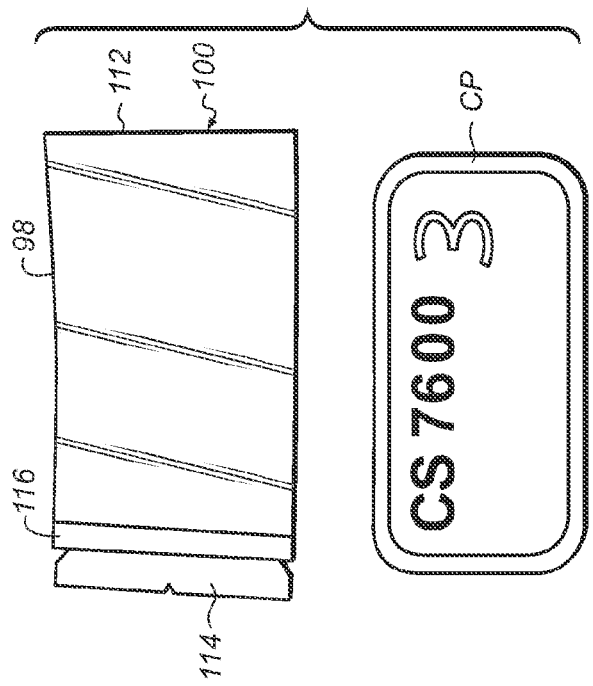

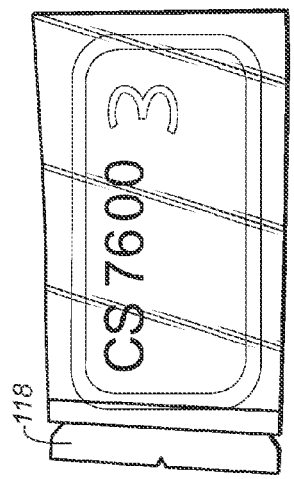
FIG. 7A
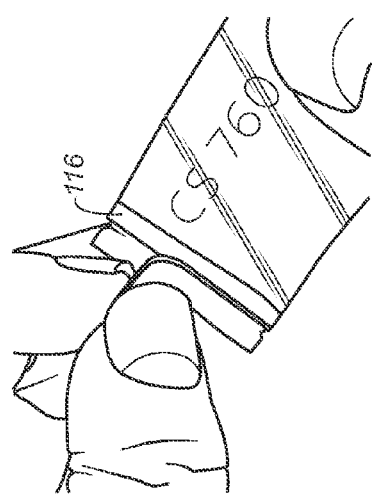
FIG. 7B
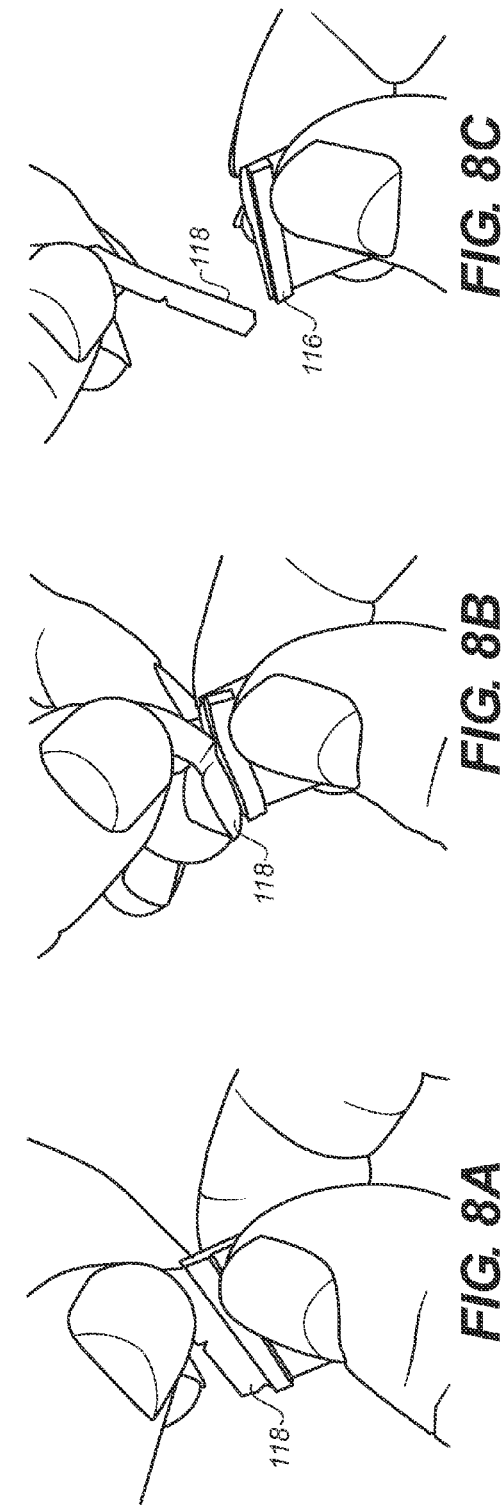
FIG. 8A
FIG. 8B
FIG. 8C

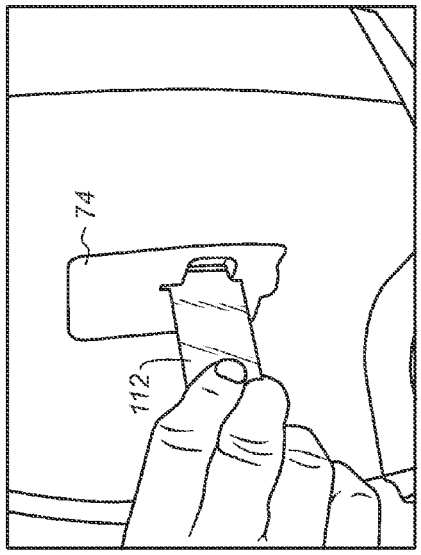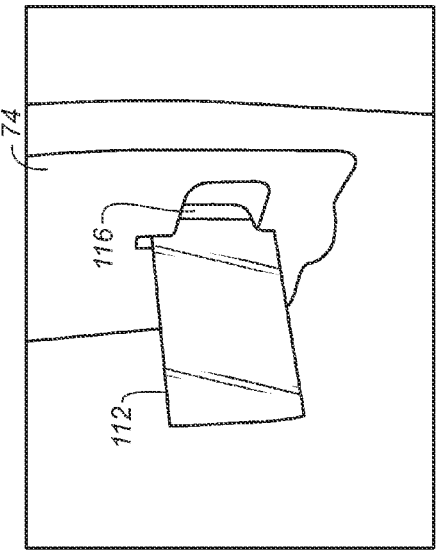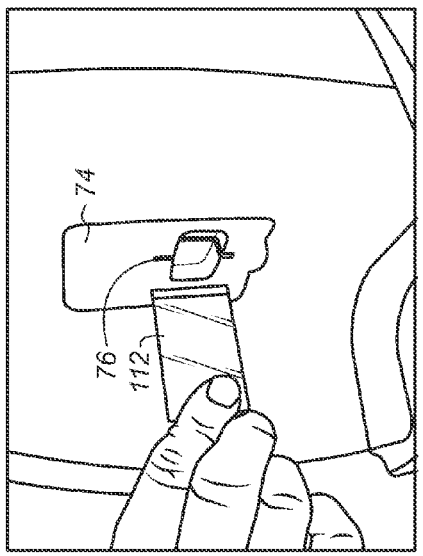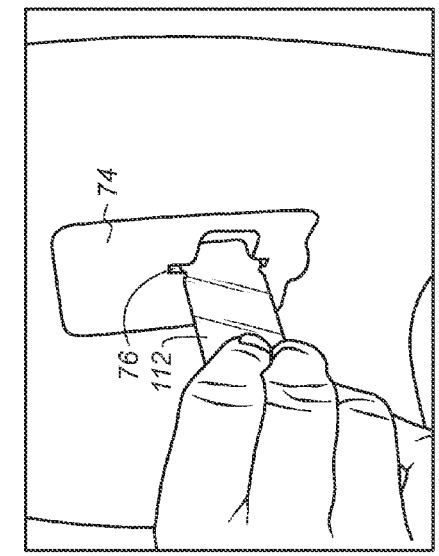

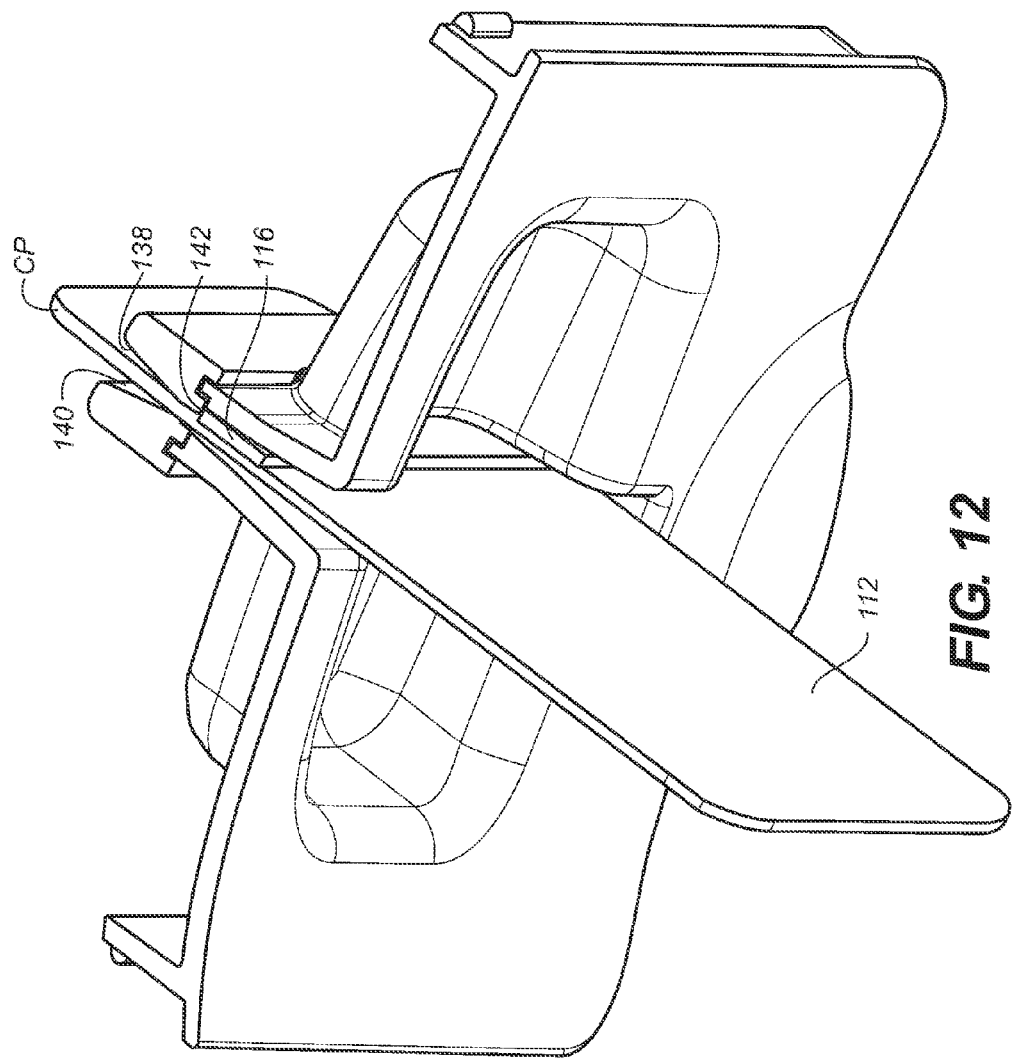

COMPUTED RADIOGRAPHY SCANNER AND ENVELOPE FOR IMAGING PLATES

FIELD OF THE INVENTION

The present invention relates to digital scanners for photostimulable phosphor imaging plates and to barrier envelopes used for containing the phosphor imaging plates during their processing. In particular, the present invention refers to digital scanners and envelopes used for processing flexible information carrier plates for intra-oral dental imaging.

BACKGROUND OF THE INVENTION

The use of information carrier plates (also referred to as phosphor or phosphor storage plates) for obtaining visually perceptible contrast upon exposure to X-rays is known in the art as computed radiography (CR) and is described for example in U.S. Pat. No. 7,211,785 (Berger).

The imaging cycle employing such plates comprises juxtaposing the plate nearby a specific part of the body (e.g., leg, arm, tooth, etc.) and then exposing the plate to X-rays in order to obtain an image from stored radiation energy. Following exposure, the plate is then removed from the patient and the plate with latent image that is stored thereon proceeds to a scanner, in which it is scanned by a laser beam or other energy source to stimulate emission of the stored energy and to form corresponding image data from the emitted energy. After the plate has been scanned, the obtained image data can be displayed and stored for further examination. The exposed and scanned plate is then erased and can be reused in a subsequent imaging cycle.

The use of computed radiography is known both in general medical applications and in dental applications. The modern digital dental systems employ intra-oral image plate scanners in which the plates are scanned after the X-ray exposure. During the X-ray exposure and after it the plates are enclosed within an envelope to prevent the patient from cross contamination and at the same time to protect the plate from saliva and from other substances in the patient's mouth. The other function of the envelope is to reduce as much as possible the exposure of the exposed plate to ambient light before it is scanned.

Various digital intra-oral image plate scanners are known in the art of intra-oral digital radiography as well as various envelopes which are used during the X-ray exposure and during the further processing.

U.S. Pat. No. 6,827,214 (Alzner) and U.S. Pat. No. 6,866,149 (Alzner) describe a barrier envelope for reusable photostimulable phosphor imaging plates. The envelope comprises of a plastic transparent film and a plastic opaque film sealed to each other about three sides of the envelope. The free side of each film is formed with a flap and one flap is coated with an adhesive medium protected by a peel strip. The envelope is provided on one side thereof with a "Y" shaped notch to facilitate tearing open of the envelope.

U.S. Pat. No. 7,649,190 (Alzner) describes a portable scanning assembly for photo-stimulatable phosphor imaging plates.

U.S. Pat. No. 7,053,396 (Alzner) describes an apparatus for retrieving information on a reusable storage film.

DE 10303001 (Thoms) describes a memory film scanner with insertion aid having a guide for a memory film which opens into input slit of memory film reader when insertion aid is mounted on reader.

U.S. 2010/0171052 (Thorns) describes a flexible foil readout device provided with cartridge shaped solid support for the foil.

Depending on specific construction of the scanner there are known various techniques for handling the plates stored in the envelopes after the X-ray exposure.

So, for example it is known to remove the exposed plate from the envelope and to reload it in a container, which prevents exposure to light before scanning. The container with the plate is transported then to the scanner and here the plate is removed from the container and is inserted in the scanner.

On the other hand it is known to remove the plates from their envelopes and to reload them into dedicated containers which then are transported to scanning location and here the containers with the plate inside are entered in the scanner.

Nevertheless despite various attempts to employ envelopes in the workflow of intra-oral digital radiography there is still need for a new, simple and convenient solution. In particular the new solution would allow insertion of the enveloped plate immediate within the scanner followed by easy and effortless extraction of the plate from the envelope and its automatic loading in the scanner.

SUMMARY OF THE INVENTION

The present invention is intended to provide simple, convenient and reliable solution for processing flexible information carrier plates used in intra-oral dental computed radiography.

An object of the present invention is to provide a new envelope and a scanner for dental radiography enabling processing flexible information carrier plates, when the plates are enclosed in disposable or in re-usable envelopes.

Another object of the present invention is to provide a new envelope and a scanner for dental computed radiography that can be used with flexible information carrier plates, irrespective of the plate size.

Still further object of the present invention is to provide a new envelope and a scanner, which enables easy and convenient insertion the enveloped plate in the scanner followed by reliable extraction of the plate from the envelope and automatic loading the plate within the scanner, while the envelope is retained outside the scanner.

Yet another object of the invention is to provide a new envelope, which allows easy and convenient loading of the plate within the envelope and fast sealing the envelope before the X-ray exposure, such that the patient is reliably prevented from cross contamination and the plate is protected from saliva and from other substances in the patient's mouth.

Still further object of the invention is to provide a new envelope, which reduces as much as possible the exposure of the plate to ambient light during transportation the enveloped plate to scanning.

Another object of the invention is to provide a new envelope which allows fast and convenient opening thereof before insertion the envelope in the scanner.

Still further object of the invention is to provide a new envelope, which manufacturing is simple and inexpensive.

According to one embodiment, the present invention concerns a scanner for processing intra-oral flexible information carrier plates exposed to X-rays and transported to the scanner being dressed in envelopes. The scanner has housing with an opening for entering an enveloped plate inside the scanner, the opening is adapted to allow exiting the plate from the envelope and passing the plate inside the housing while the opening is adapted to retain the envelope outside the housing.

The present invention refers also to an envelope for intra-oral flexible information carrier plate which is intended upon exposure to X-rays to be transported to a scanner for digital radiography processing. The envelope comprises a frontal and rear layer defining a compartment for enclosure the plate inside. The envelope comprises a protrusion, which upon entering an enveloped plate inside the scanner is adapted to allow exiting the plate from the envelope and passing the plate inside the scanner while retaining the envelope outside the scanner.

For a better understanding of the present invention as well of its benefits and advantages, reference will now be made to the following description of various exemplary embodiments taken in combination with the accompanying drawings.

BRIEF DESCRIPTION OF THE DRAWINGS

FIG. 5 depicts schematically an envelope according to an embodiment of the present invention.

FIGS. 6A, 6B and 6C show various stages of insertion of a flexible carrier plate into envelope shown in FIG. 5.

FIGS. 7A and 7B show respectively sealing of the envelope and the sealed envelope before X-ray exposure.

FIGS. 8A, 8B and 8C show opening the envelope before inserting it into scanner shown in FIG. 4.

FIGS. 9A, 9B, 9C and 9D show various stages of insertion of the envelope with the plate within the scanner.

FIG. 12 shows the envelope retaining outside the scanner while the plate exits from the envelope.

DETAILED DESCRIPTION OF THE INVENTION

It is noted that the present invention is not limited to computed medical radiography in general or to intra-oral dental radiography in particular. The present invention is suitable for other medical and non-medical applications as well.

In the context of the present disclosure, the equivalent terms "flexible information carrier plate", "flexible plate", "CR plate", "carrier plate" or simply "plate" refer to photo-stimulable phosphor plates (PSP plates) that are used for image storage in the computed radiography CR arts, deployed in a manner analogous to the photographic plates that they have replaced in many applications. The information carrier plate is considered flexible when it has at least some degree of conformance to curvatures useful for intra-oral imaging.

In the context of the present disclosure, the term "scanner" or "scanning device" refers to a device or apparatus that is capable of obtaining stored image data from the flexible information carrier plate following exposure of the plate. The scanner typically stimulates the phosphor storage media using a laser beam. As the beam energy passes over the plate surface, it frees electrons "trapped" in "color centers" in the crystal lattice of the X-rayed phosphor plate. The light emitted during laser stimulation can be collected and the resulting signal converted into a digital image by a computer or other dedicated logic processor. The location at which the scanner is deployed is referred to as a "scanning station".

Figure 1:
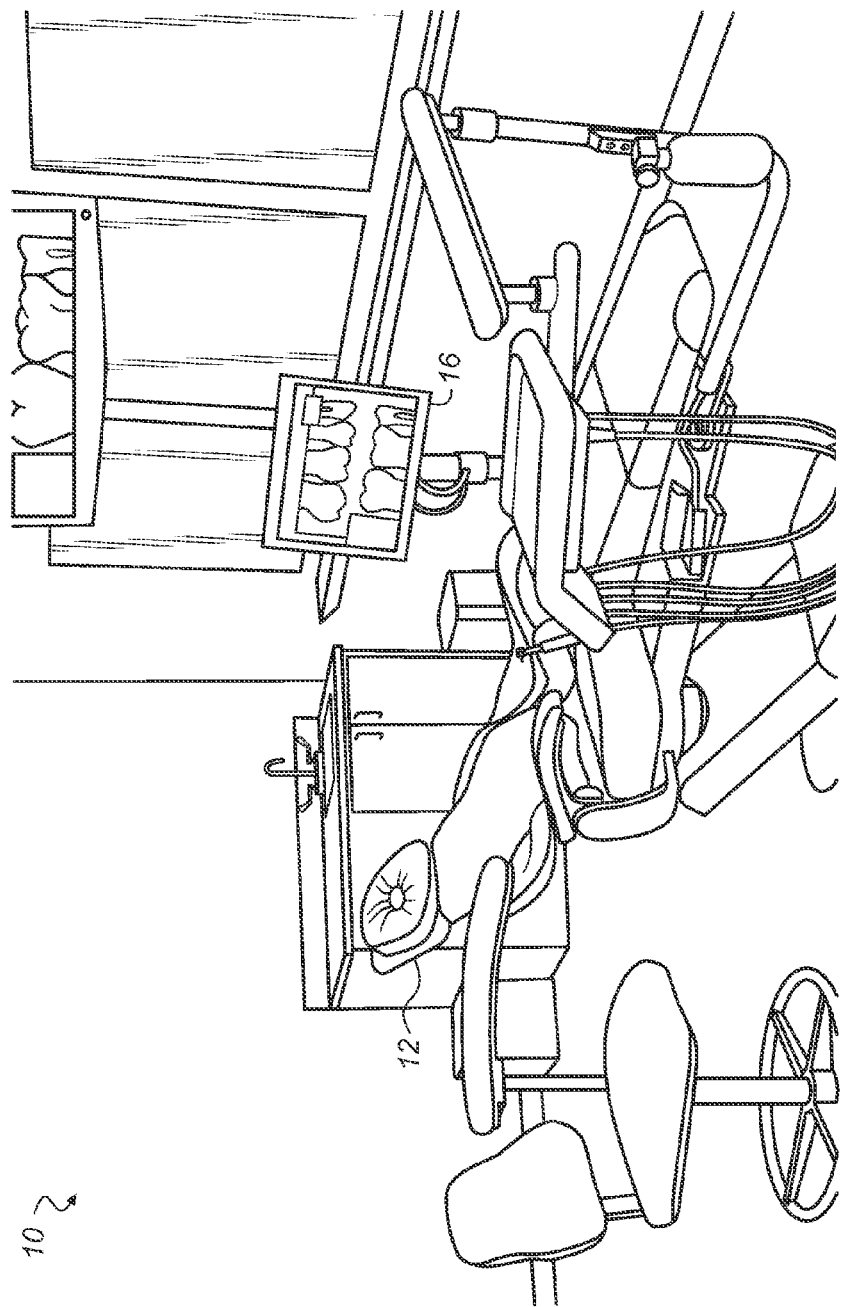
FIG. 1 shows a general treatment room used by a practitioner and provided with a chair working station.

Referring now to FIG. 1, there is shown a typical dental treatment room 10 of a practitioner. The treatment room inter alia comprises a treatment chair 12 having a console with various instruments as required for dental treatment, e.g. intra-oral treatment.

The treatment room is preferably equipped with a suitable interface terminal that serves as a processing and acquisition station for input, output, and management of data and possibly including a keyboard with a mouse. It is not shown specifically but should be appreciated that the interface communicates over a network, for example, via a local Ethernet network, with a suitable server providing access to a database and a software application enabling management of medical and personal data related to a medical case. The application also allows acquisition, viewing, and processing of images obtained after scanning, archiving the images and related data, and other functions. In an alternate embodiment, such as in a small clinic, the interface may communicate with a local computer workstation or personal computer (PC), instead of with a networked server.

The treatment room is suitable for computed intra-oral dental radiography and is equipped with a monitor 16, e.g., a LCD (Liquid Crystal Display) for displaying images acquired after X-ray exposure and scanning. It is not shown in FIG. 1 but should be appreciated that a plurality of flexible information carrier plates are available, typically stored in the vicinity of the treatment chair.

While not shown in FIG. 1, it would be appreciated that the treatment room can also comprise an X-ray generator, which may be situated either in the treatment room itself or adjacent thereto. In a small treatment room, a scanner can also be provided for obtaining the stored image data obtained after exposing the information carrier plates to X-rays. However location within the treatment room is not compulsory, since the practitioner can alternately use a scanner that is situated apart from the treatment room.

In the present disclosure, the treatment room is alternately referred to as a working station.

Figure 2:
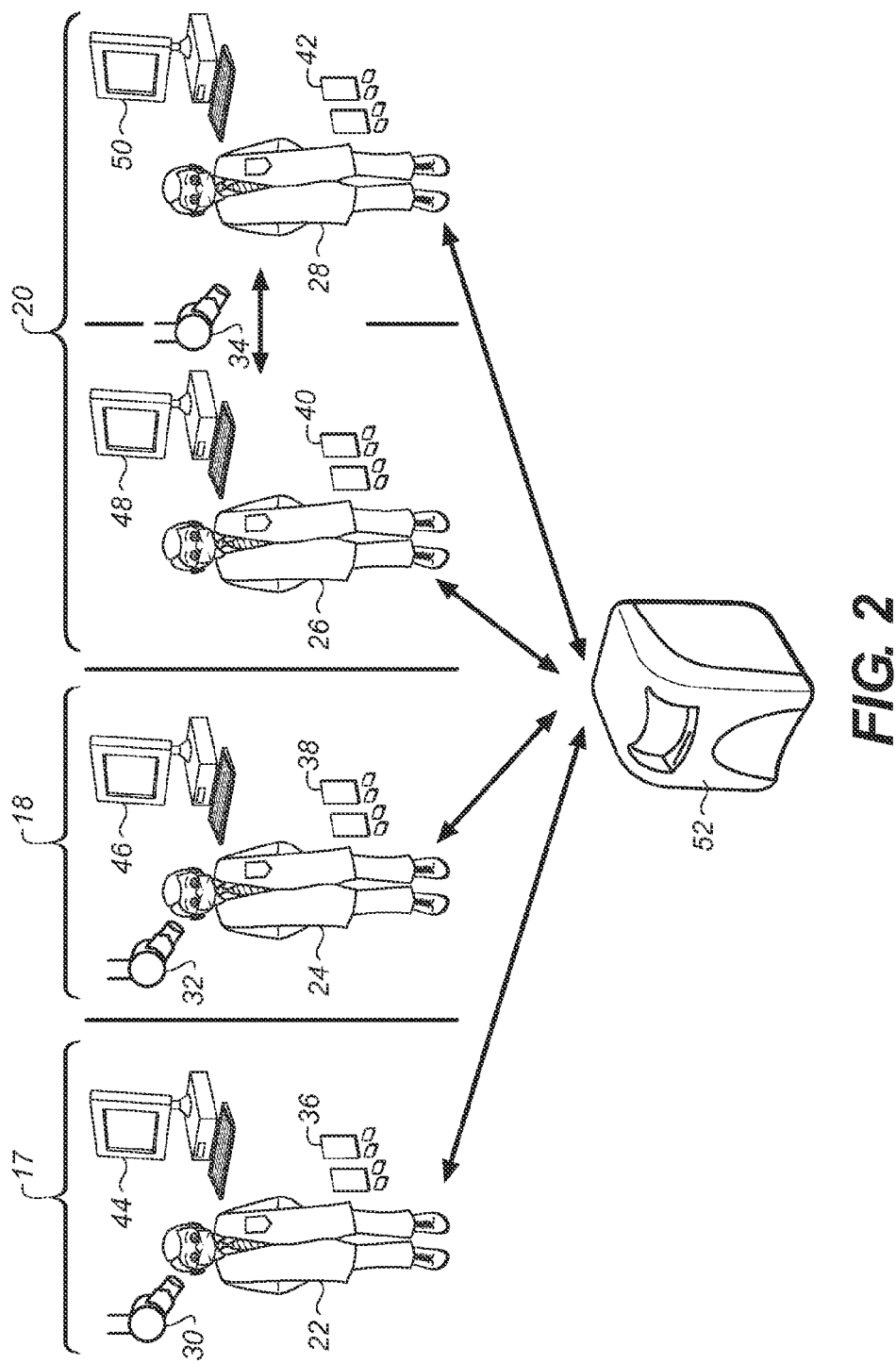
FIG. 2 depicts examples of working environment in which several practitioners occupy separate working stations and share the same scanning station.

FIG. 2 shows a schematic of another exemplary working environment for intra-oral computed radiography. This working environment comprises a plurality, for example three, separate working stations 17, 18, 20. Working stations 17 and 18 are used by two respective practitioners 22 and 24. Working station 20 is used by two neighboring practitioners 26 and 28. Each working station is equipped with a respective X-ray generator 30, 32, 34. The generator 34 is shared by practitioners 26 and 28.

Each practitioner has sufficient stock 36, 38, 40, 42 of flexible information carrier plates, here designated as media. Each working station has a computer with respective LCD monitor 44, 46, 48, 50 and respective keyboard and mouse.

Figure 3:
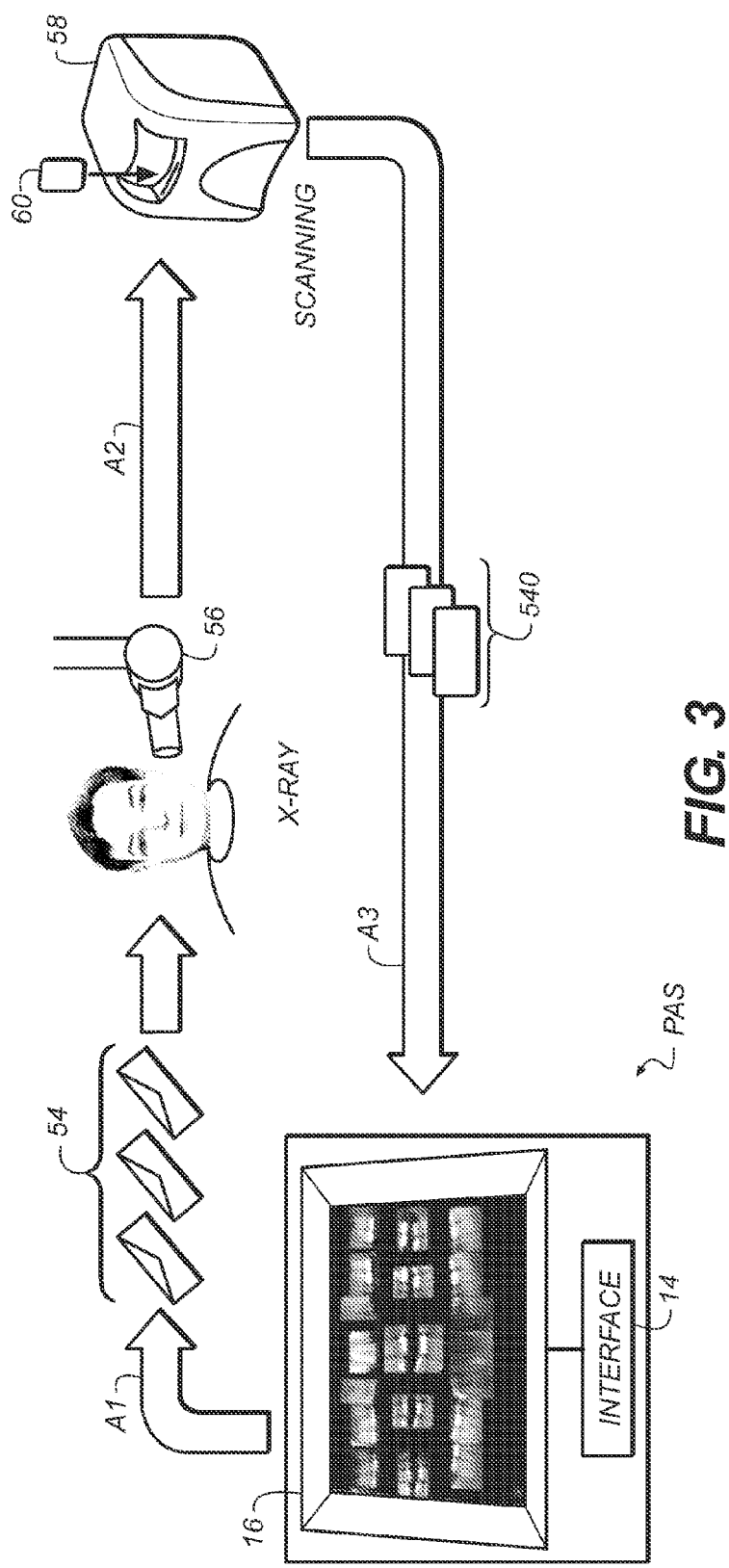
FIG. 3 shows a working cycle of intra-oral computed radiography during which flexible carrier plates are scanned at the scanning station.

It is also seen in FIG. 2 that all working stations communicate with a common scanner 52. This scanner is shared by all practitioners and therefore, in order to organize the workflow efficiently, the scanning step should be synchronized with the X-ray exposure step so that each practitioner reserves the scanner for plate processing before sending the exposed plates to scanning. In FIG. 3 is depicted an example of a working cycle suitable for information carrier plates in accordance with an embodiment of the present invention. A processing and acquisition station (PAS) has an interface 14 coupled with monitor 16 on which are displayed images acquired during previous scanning. It is seen also that a plurality of intra-oral information carrier plates 54, enclosed in envelopes, proceed as shown by arrow A1, from the processing and acquisition station to X-ray generator 56. The plates intended for exposure are not yet imaged, with any previously obtained image erased from their surface after previous scanning. The plates being dressed in the envelopes are put in the mouth of a patient nearby the teeth to be examined. Upon completing X-ray exposure, the plates pass, as shown by an arrow A2, to the scanning station for scanning in a scanner 58. By virtue of the present, as it will be explained in more details further, the plates are not removed from the envelopes before scanning, as known in the prior, art but are inserted in the scanner being still dressed in the envelopes. One such envelope with the plate placed therein is designated by numeral 60 and it is shown being ready for insertion into the entry slot of the scanner. It is not shown in FIG. 3 but should be appreciated that after insertion the envelope into entry slot of the scanner the image plate exits from the envelope and enters inside the scanner, while the envelope remains outside the scanner. As soon as the plate enters the scanner it is picked up by a carrier mechanism provided in the scanner, which transports the plate from the entry slot to the scanning position. Upon completing scanning, the plate is erased, exits the scanner and proceeds back to the processing and acquisition station. Erased plates without envelopes are generally illustrated as 540. FIG. 3 shows schematically a plurality of erased undressed plates proceeding back to the processing and acquisition station as indicated by an arrow A3. At the working station, the erased plates are again dressed into fresh disposable envelopes and are ready for the next working cycle.

Figure 4:
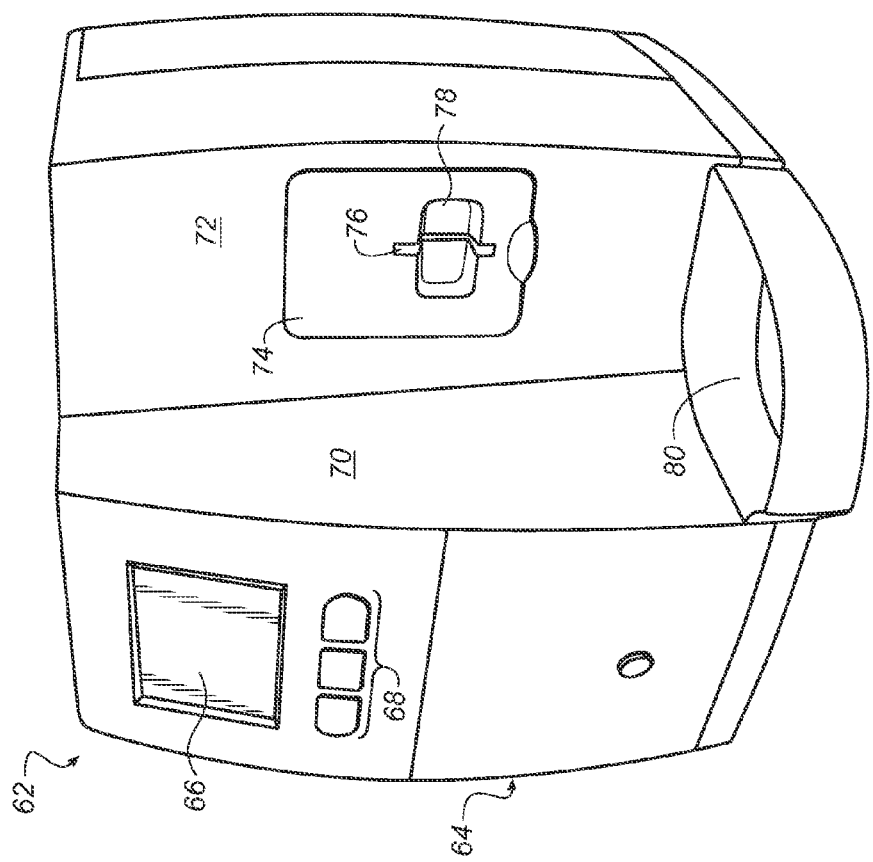
FIG. 4 depicts schematically a scanner used for intra-oral computed radiography in accordance with the present invention.

The present invention is suitable for example for use with the flexible carrier plates provided with a RFID tag, since the plates can be tagged while enclosed in envelopes With reference to FIG. 4, an embodiment of a scanner 62 for intra-oral computed radiography in accordance with the present invention will be explained. In this embodiment the scanner is provided with a housing 64 configured as a parallelepiped. The housing is manufactured from a suitable plastic material. The housing has a frontal face on which are disposed a display screen 66 and control knobs 68. As seen in FIG. 4, one of the corners of the housing is recessed by a couple of intersecting faces 70, 72. On the face 72 is disposed an entrance panel 74 having an entry slot 76. The entrance panel is provided with a depression 78 for more convenient entering envelopes of small sizes in the entry slot. It will be explained further with reference to FIGS. 10-13 that at least a portion of the entry slot is provided with an abutment plane, serving as a barrier, which prevents the envelope entering inside the scanner, while exit of the plate from the envelope and its entering in the scanner is enabled. At the lower part of the housing a tray 80 is provided, in which are collected empty envelopes remaining outside the scanner after the plates enter inside the scanner.

It is noted that the scanner could be provided with the housing configured not as shown in FIG. 4 but with some other shape. Furthermore, it is not shown specifically, but could be appreciated by one skilled in the art, that within the housing are provided the necessary components and mechanisms, which are usually required for normal operation of the scanner.

Referring to FIG. 5, an embodiment of the envelope of the present invention will be now described. FIG. 5 shows an envelope 82 configured as a sachet having generally rectangular outside contour with rounded corners. The envelope's outside contour is defined by opposite long sides 84, 86, opposite short sides 88, 90 and rounded corners R1, R2, R3, R4.

The envelope is provided with the outside contour which shape and dimensions conforms the shape and dimensions of a carrier plate that has to be inserted within the envelope. In practice, for example, dimensions of the envelope for a carrier plate No. 2 are as follows: length of the long side is 49.0 mm, length of the short side 36.0 mm and corner radius 6.5 mm, while length of the long side of the carrier plate is 41 mm and length of the short side of the carrier plate is 31.0 mm.

The envelope is preferably formed from two layers of plastic material, which are sealed along the sides 84, 86, 88, while the layers are not sealed along the side 90, such that a border line 92 is provided delimiting a compartment 94 into which a carrier plate CP can be inserted through the open side 90. The compartment is delimited by a sealing margin SM and by the border line which shape conforms to the outside contour of the envelope. The width dimension W of the sealing margin should be selected in such a manner that the border line is located at a small distance from the carrier plate CP, which contour is shown by a line 96. By virtue of this provision the carrier plate is not too tightly retained within the envelope and can effortlessly leave the compartment. In practice the distance between the border line and contour of the carrier plate CP is about 1 mm.

Referring to FIGS. 6A, 6B, 6C, it is shown a rear layer 98 and a frontal layer 100 sealed along three sides such that a compartment is provided into which carrier plate CP is accommodated. The rear layer can be comprised of an opaque vinyl or similar plastic material, while the frontal layer can be translucent vinyl or similar plastic material. The rear layer could contain also a pigment to control the opacity.

The carrier plate is placed in the envelope in such a manner that the X-ray exposed side faces the opaque rear layer, while the not exposed side bearing various indicia referring to the plate, faces the translucent frontal layer. By virtue of this provision the plate when inserted in the envelope can be easily identified and at the same time its exposed side is prevented from exposing to light.

The overall thickness of the envelope with the carrier plate inside is about 1.5 mm.

Referring to FIG. 5 it is seen that directed parallel to the short side 90 of the envelope a peel strip 102 is provided. This strip coats a location 104 of the rear layer, which is covered by an adhesive. The function of the peel strip is to expose location 104 and to enable sealing the envelope when the carrier plate is inserted there into.

Beneath the peel strip and on the frontal layer, a protrusion region 106 is provided, which transversally extends from one long side of the envelope to the opposite long side. The protrusion can be made of a soft material and is permanently secured on the frontal layer by an adhesive. The protrusion can be configured as a strip having width of about 5.0 mm and height H of about 0.8 mm. As an example of a suitable material for the protrusion one can mention foamed material Bisco HT-820 manufactured by Roogers Co. An example of a suitable adhesive material is double coated tape 300LSE 947 4LE manufactured by 3M Company. The function of the protrusion is to prevent advancing the envelope into scanner when the envelope with the carrier plate inside is inserted in the entry slot of the scanner.

It is illustrated in FIG. 5 that on opposite long sides of the envelope, and preferably between the peel strip and protrusion region, there are V-shaped notches 108, 110, whose function is to facilitate tearing of the sealed region of the envelope to enable exit of the carrier plate from the envelope.

In FIGS. 6A, 6B, 6C, 7A, 7B there is illustrated how a carrier plate CP is placed in an envelope and then the envelope is sealed. This stage of the working cycle takes place before exposing the plate to X-rays. In the figures is shown an envelope 112 with peel strip 114 and protruding region 116. FIG. 7B illustrates an envelope with carrier plate inside. The envelope is sealed along an adhesive region 118.

The envelope shown in FIGS. 6A, 6B, 6C, 7A and 7B is suitable for carrier plate No. 3 which indicia are seen through translucent frontal layer. Opaque black rear layer of the envelope is seen as a black margin around the translucent frontal layer.

It can be appreciated that this is only an example and that either smaller or larger carrier plates could be entered in similarly configured envelopes having suitable dimensions and provided with peel strip and protruding region.

In practice all conventional plates with standard intra-oral sizes 0, 1, 2, 3, 4, 5 can be used with the envelope and scanner of the present invention.

In FIGS. 8A, 8B and 8C is shown still further stage of the working cycle, when the carrier plate has been already exposed to X-rays and now it is ready to be scanned. Before insertion of the envelope with the plate into scanner a technician tears by fingers sealed region 118 to enable extraction of the plate from the envelope.

Another step is depicted in FIGS. 9A-9D showing how a technician inserts envelope 112 into entry slot 76 made in entrance panel 74 of the scanner. The envelope is held at its rear end and gently pushed into the slot such that it gradually enters therein as shown in FIGS. 9A-9C. The envelope is pushed into the slot until position shown in FIG. 9D. In this position protruding region 116 prevents further advancement of the envelope into slot.

Figure 10:
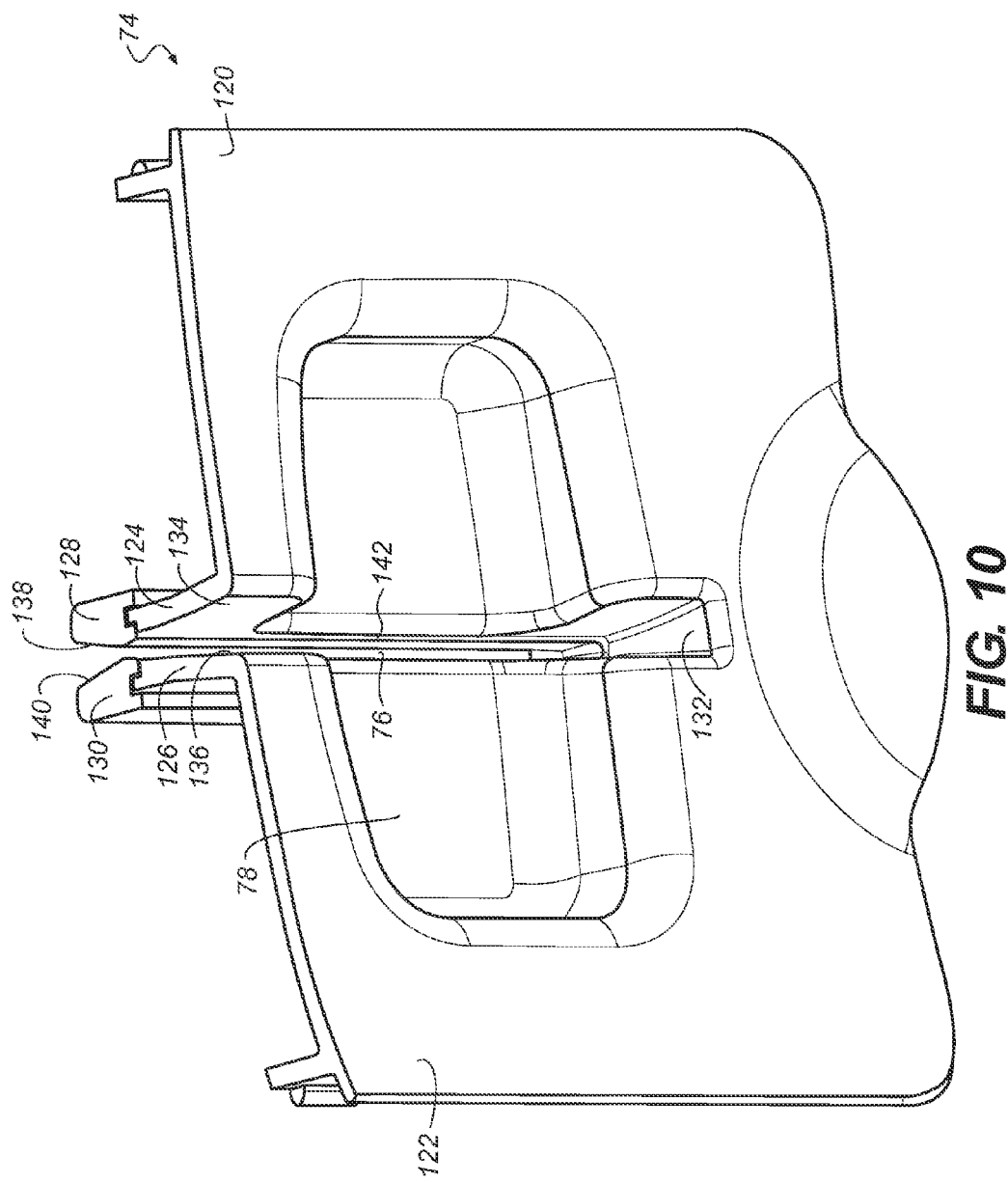
FIG. 10 shows enlarged image of an entrance plate of the scanner shown in FIG. 4.

Referring to FIG. 10, construction of an entrance panel will now be described. The entrance panel is manufactured from a plastic material and is shaped as a substantially flat body divided by slot 76 into a right wing 120 and a symmetrical left wing 122. The middle region of the entrance panel is provided with a depression or cavity 78 configured and dimensioned to enable convenient handling of the envelope when it is entered in the entry slot.

The right wing and the left wing is formed with a corresponding symmetrical right and left front guiding portion 124, 126 and with a right and left rear guiding portion 128, 130. The guiding portions are directed substantially vertically and they are connected through a common floor section 132. The guiding portions are provided with respective guiding faces, which together with floor section define the entry slot.

As seen in FIG. 10, the right front guiding portion 124 is delimited by a right front guiding face 134, the left front guiding portion 126 is delimited by a left front guiding face 136, the right rear guiding portion 128 is delimited by a right rear guiding face 138 and the left rear guiding portion 130 is delimited by a left rear guiding face 140.

The front and rear guiding faces are directed with respect to each other such that they are in a V-shaped disposition, in the sense that front guiding faces 134, 136 diverge in a front direction and rear guiding faces 138, 140 diverge in a rear direction. Here by the front direction is meant direction from the scanner outside and by the rear direction is meant direction from outside into scanner.

It can be appreciated that due to the V-shaped disposition of the guiding faces the slot has varying width, which is wider at the slot entrance and at the slot exit, while it is narrower there-between. By virtue of this provision insertion of the envelope into slot and entrance of the plate into scanner is facilitated.

It is also seen in FIG. 10, that the left front guiding face 136 is flush with the left rear guiding face 140, while the right front guiding face 134 is not flush with the right rear guiding face 138, such that a shoulder is provided, or barrier having a face 142 extending vertically along the rear guiding portion. In practice the guiding portions are dimensioned and configured in such a manner that the width of the shoulder face 142 is about 0.8 mm.

Figure 11B:
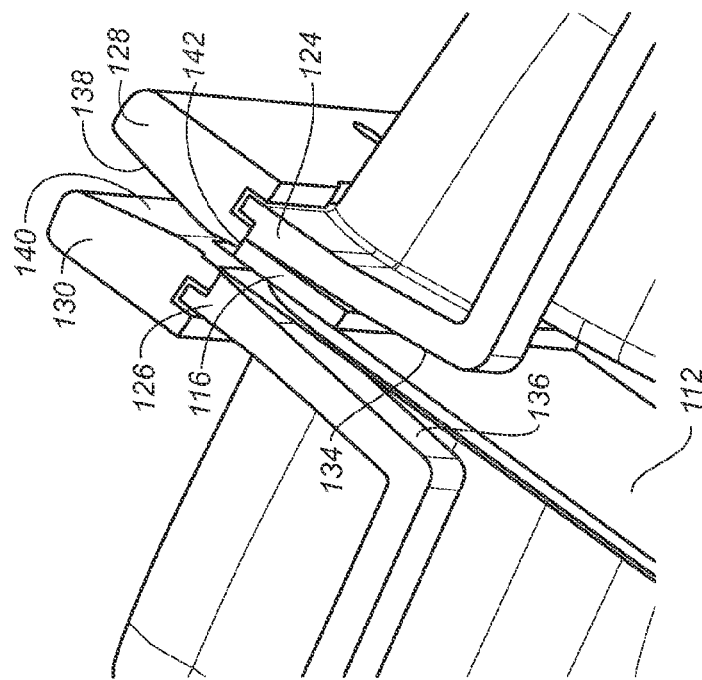
FIGS. 11A and 11B are enlarged images of the entrance plate and the envelope showing how the envelope is retained outside the scanner when the plate is ready to exit from the envelope.
Figure 11A:
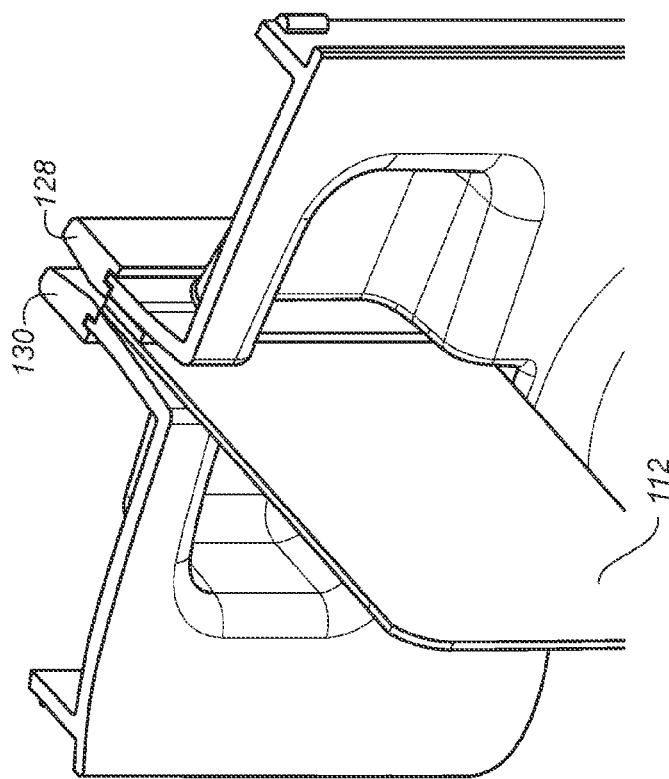

Referring to FIGS. 11A, 11B and 12 it is seen envelope 112 after it has been pushed inside the entry slot until protruding region 116 places against shoulder face 142. In this position the shoulder functions as a barrier and its face 142 prevents further advancement of the envelope, while extraction of the carrier plate CP from the envelope is possible. Seeing that the protruding region is made of soft material the contact between the protruding region and the shoulder face does not deteriorate alignment of the envelope and the entry slot, such that when technician keeps holding the rear end of the envelope the carrier plate easily passes between rear guiding portions 138, 140 inside the scanner. This situation is depicted in FIG. 12. It is not seen in FIG. 12 but should be appreciated that the envelope after the plate has been extracted there-from falls down into collecting tray. The used envelopes collected in the tray are exposed.

The carrier plate after it has been fully extracted from the envelope enters the scanner where it is picked up by a dedicated driving mechanism (not shown), e.g. driving rollers, which advance the plate to a scanning position. Upon completing the scanning and acquiring the image the carrier plate is erased and exits from the scanner. It can be redressed into fresh envelope and used in a new working cycle.

By providing the envelope with a protruding region and the scanner entry slot with a barrier it is possible to easily, conveniently and hygienically handle the carrier plates between the X-ray exposure station and scanning station without extracting them from the envelopes and without reloading them into auxiliary boxes, cassettes, cartridges or other receptacles.

The plates inserted into envelopes are not exposed to light, are easily recognizable and their correct orientation for insertion into entry slot can't be mixed up.

The envelope has a construction which can be readily manufactured from conventional plastic materials.

The invention has been described in detail with particular reference to certain preferred embodiments thereof, but it will be understood that variations and modifications can be effected within the scope of the invention.

For example, in one embodiment, the entrance plate can be manufactured not separate from the housing so as to be securable thereon but be an integral part of the scanner housing.

The shoulder face can extend not along the full length of the entry slot but along a portion thereof.

Similarly the protruding region provided on the front layer of the envelope can be manufactured integrally therewith and it is not necessary that it protrudes along the full width of the envelope.

Thus, a new envelope and a scanner are provided for identification, monitoring, and tracking of flexible information carrier plates used in intra-oral dental computed radiography.

The invention claimed is:

1. A scanner for processing intra-oral flexible carrier plates exposed to X-rays and transported to the scanner being dressed in envelopes, each of the envelopes having a protrusion on an outer surface, the scanner having a housing with an opening for entering an enveloped plate inside the scanner, wherein the opening is configured as an entry slot having a barrier, wherein the protrusion on the envelope engages the barrier to prevent entrance of the envelope inside the housing while allowing the plate to exit from the envelope and passing the plate inside the housing.

2. The scanner according to claim 1, wherein the barrier is configured as a shoulder provided in the entry slot.

3. The scanner according to claim 2, wherein the entry slot is delimited by a left front guiding face, by a right front guiding face, by a left rear guiding face, and by a right rear guiding face.

4. The scanner according to claim 3, wherein a distance at least between left front guiding face and right front guiding face is variable.

5. The scanner according to claim 1, wherein the housing is provided with an entrance panel and the opening is made in the entrance panel.

6. The scanner according to claim 5, wherein the entrance panel is secured on the housing.

7. The scanner according to claim 3, wherein the left front guiding face and the right front guiding face are spaced apart by at least a first distance is sufficient for passing the enveloped plate, while the left rear guiding face and the right rear guiding face are spaced apart by at least a second distance sufficient for passing only the carrier plate.

8. The scanner according to claim 2, wherein the shoulder is defined by a face extending along at least a portion of the entry slot.

9. The scanner according to claim 7, wherein a barrier face is provided at one of the rear guiding faces.

10. The scanner according to claim 8, wherein the face has a width of about 0.8 mm.

11. An envelope for an intra-oral flexible information carrier plate which is intended upon exposure to X-rays to be transported to a scanner for digital radiography processing, the envelope comprising a frontal and rear layer defining a compartment for enclosing the plate inside and having an outer surface, the envelope having a protrusion on the outer surface, which upon entering an enveloped plate inside the scanner through a scanner opening is adapted to engage the opening to allow exiting the plate from the envelope and passing the plate inside the scanner while retaining the envelope outside the scanner.

12. The envelope according to claim 11, wherein the frontal layer is made of a translucent material, while the rear layer is made of an opaque material and the protrusion is located on the frontal layer.

13. The envelope according to claim 12, wherein the protrusion is configured as a strip.

14. The envelope according to claim 13, wherein the strip is made of a soft material.

15. The envelope according to claim 14, wherein the strip has a thickness of about 0.8 mm.

16. The envelope according to claim 13, wherein the protrusion is adhered to the frontal layer.

17. The envelope according to claim 11, wherein the envelope is provided with a peel strip covering a portion of the rear layer, which is coated by an adhesive.

18. The envelope according to claim 17, wherein the envelope is provided with at least one notch.

* * * * *